US009987658B1

(12) United States Patent
Rolin et al.

(10) Patent No.: US 9,987,658 B1
(45) Date of Patent: Jun. 5, 2018

(54) METHOD OF MANUFACTURING A HUMIDITY SENSING MATERIAL

(71) Applicant: The United States of America as Represented by the Administrator of the National Aeronautics and Space Administration, Washington, DC (US)

(72) Inventors: Terry D. Rolin, Elkmont, AL (US); Ian K. Small, Huntsville, AL (US)

(73) Assignee: The United States of America as represented by the Aministrator of the National Aeronautics and Space Administration, Washington, DC (US)

( * ) Notice: Subject to any disclaimer, the term of this patent is extended or adjusted under 35 U.S.C. 154(b) by 0 days. days.

(21) Appl. No.: 15/473,322

(22) Filed: Mar. 29, 2017

(51) Int. Cl.
*B05D 3/02* (2006.01)
*C04B 35/468* (2006.01)
(Continued)

(52) U.S. Cl.
CPC .......... *B05D 3/0254* (2013.01); *B05D 3/048* (2013.01); *B05D 3/0413* (2013.01); *B05D 3/0493* (2013.01); *C04B 35/4682* (2013.01); *C04B 35/6262* (2013.01); *C04B 35/6264* (2013.01); *C04B 35/62222* (2013.01); *C04B 35/6303* (2013.01); *C04B 35/64* (2013.01); *G01N 27/223* (2013.01); *G01N 27/226* (2013.01); *C04B 2235/3215* (2013.01);
(Continued)

(58) Field of Classification Search
CPC .... B05D 3/0254; B05D 3/0413; B05D 3/048; B05D 3/0493; C04B 35/4682
See application file for complete search history.

(56) References Cited

U.S. PATENT DOCUMENTS 6,202,471 B1   3/2001   Yadav et al.
6,946,197 B2   9/2005   Yadav et al.
(Continued)

FOREIGN PATENT DOCUMENTS

JP       58142252 A   *   8/1983

OTHER PUBLICATIONS

Vijatovic et al., Properties of lanthanum doped BaTiO(3) produced from nanopowders, Ceramics International 36, 2010, pp. 1817-1824.
(Continued)

*Primary Examiner* — Nathan H Empie
(74) *Attorney, Agent, or Firm* — James J. McGroary; Mark P. Dvorscak

(57) ABSTRACT

A method is provided for manufacturing a humidity sensing material. Particles of a trivalent rare earth hydroxide or oxide (such as lanthanum hydroxide) are mixed with particles of barium oxide and titanium dioxide in specified proportions. The particle mixture is heated to generate a sintered mixture that is milled. The resulting milled particles are mixed with glass particles, an organic surfactant, a solvent, an organic vehicle, and an alkali hydroxide. The resulting liquid mixture is deposited as a layer thereof onto a substrate. The substrate and layer thereon are processed to remove liquid portions of the liquid mixture. Such liquid removal processing includes at least one cycle of heating the layer followed by a corresponding cycle of cooling the layer in a nitrogen atmosphere containing less than 25 parts per million of oxygen.

27 Claims, 3 Drawing Sheets

(51) Int. Cl.
    *C04B 35/626*     (2006.01)
    *C04B 35/63*     (2006.01)
    *C04B 35/622*     (2006.01)
    *C04B 35/64*     (2006.01)
    *G01N 27/22*     (2006.01)
    *B05D 3/04*     (2006.01)

(52) U.S. Cl.
    CPC ............ *C04B 2235/3227* (2013.01); *C04B 2235/3236* (2013.01); *C04B 2235/36* (2013.01); *C04B 2235/5436* (2013.01); *C04B 2235/656* (2013.01); *C04B 2235/6581* (2013.01)

(56) References Cited

U.S. PATENT DOCUMENTS

| | | | | |
|---|---|---|---|---|
| 2002/0022569 | A1* | 2/2002 | Takai | C01F 17/0043 |
| | | | | 501/152 |
| 2002/0025439 | A1* | 2/2002 | Ueda | B32B 18/00 |
| | | | | 428/428 |
| 2003/0100438 | A1* | 5/2003 | Kuo | C04B 35/4682 |
| | | | | 501/137 |

OTHER PUBLICATIONS

Ramoska et al., Dielectric investigations of La-doped barium titanate, Processing and Applications of Ceramics 4 [3], 2010, pp. 193-198.
Tsur et al., How Trivalent Amphoteric Dopants in BaTiO(3) Ceramics Improve Reliability of Capacitors, Center for Dielectric Studies, Materials Research Laboratory, The Pennsylvania State University.

* cited by examiner

METHOD OF MANUFACTURING A HUMIDITY SENSING MATERIAL

ORIGIN OF THE INVENTION

The invention described herein was made by employees of the United States Government and may be manufactured and used by or for the Government of the United States of America for governmental purposes without the payment of any royalties thereon or therefor.

BACKGROUND OF THE INVENTION

1. Field of the Invention

This invention relates to humidity sensing materials. More specifically, the invention is a method of manufacturing a material that is sensitive to changes in humidity where such changes manifest themselves as an electrical property.

2. Description of the Related Art

High humidity levels can negatively affect a wide variety of electronic devices. Accordingly, many electronic devices include some type of humidity sensing capability. As electronic devices continually decrease in size, so must the humidity sensors used therewith.

SUMMARY OF THE INVENTION

Accordingly, it is an object of the present invention to provide a humidity sensing material.

Another object of the present invention is to provide a humidity sensing material that is highly sensitive to changes in humidity even when only small amounts of the material are used.

Still another object of the present invention is to provide a method for manufacturing a humidity sensing material.

Other objects and advantages of the present invention will become more obvious hereinafter in the specification and drawings.

In accordance with the present invention, a method is provided for manufacturing a humidity sensing material. An embodiment of the present invention uses particles of lanthanum hydroxide having an average grain diameter of 50-700 nanometers, particles of barium oxide having an average grain diameter of 50-700 nanometers, and particles of titanium dioxide having an average grain diameter of 50-700 nanometers. The particles are mixed in a proportion defined by 0.7-5.0 weight percent of lanthanum hydroxide, 60-65 weight percent barium oxide, and a remaining weight percent titanium dioxide. The mixture of particles is heated to a temperature in a range of 1000-1300° C. wherein a sintered mixture is generated. The sintered mixture is milled to generate milled particles having diameters of 50-700 nanometers. A 50-70 weight percent of the milled particles is mixed with 5-15 weight percent of glass particles having a particle size of 0.5-10 micrometers, 0.1-5.0 weight percent of an organic surfactant, 5-25 weight percent of a solvent, 5-25 weight percent of an organic vehicle, and 1-5 weight percent of an alkali hydroxide.

The resulting liquid mixture is deposited as a layer thereof onto a substrate. The substrate and layer thereon are processed to remove liquid portions of the liquid mixture. Such liquid removal processing includes at least one cycle of heating the layer to a temperature in a range of 850-900° C. followed by at least one cycle of cooling the layer in a nitrogen atmosphere containing less than 25 parts per million of oxygen.

BRIEF DESCRIPTION OF THE DRAWING(S)

Other objects, features and advantages of the present invention will become apparent upon reference to the following description of the preferred embodiments and to the drawings, wherein corresponding reference characters indicate corresponding parts throughout the several views of the drawings and wherein.

Figure 3:
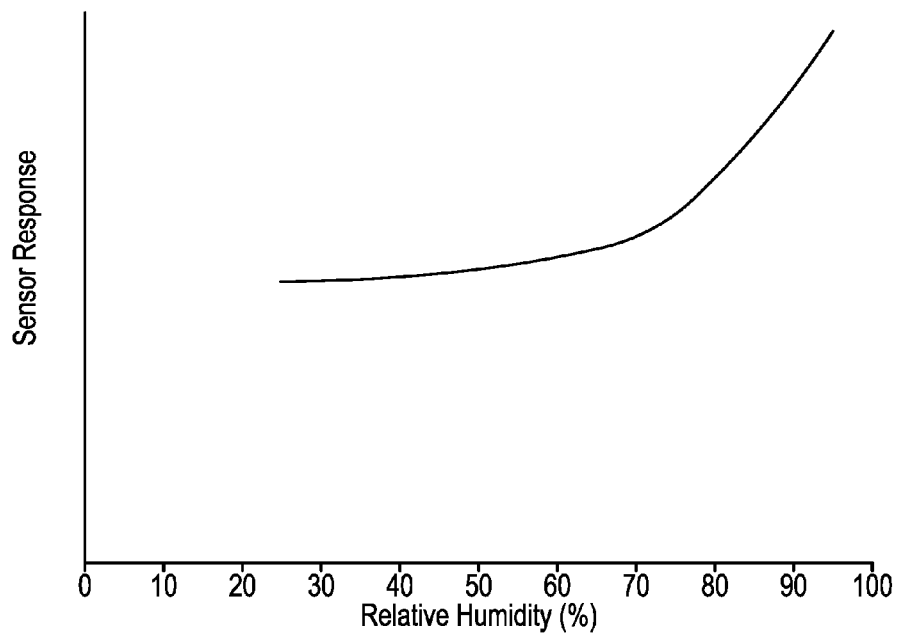
Figure 4:
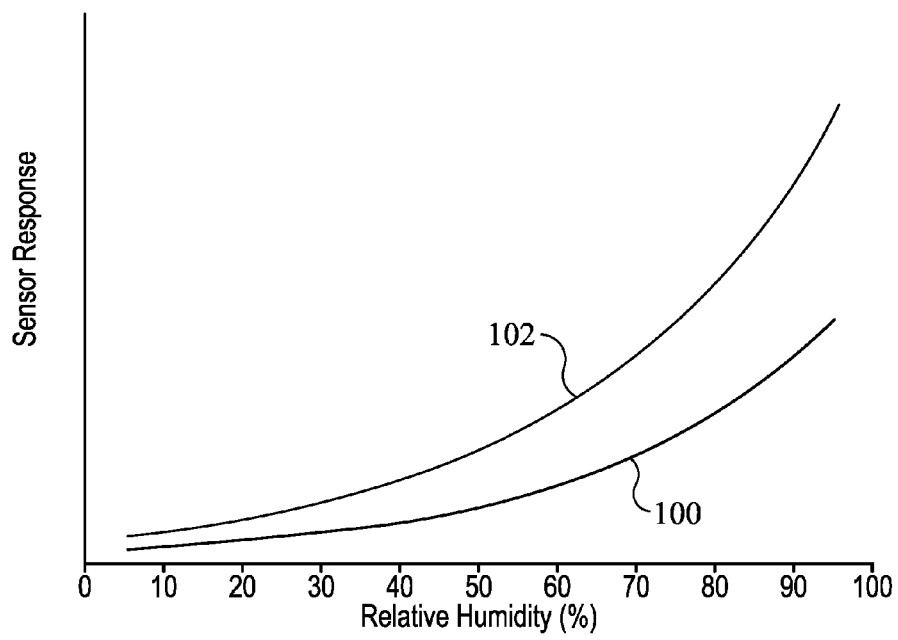

FIG. 3 is a plot of sensor response as a function of relative humidity for a plurality of operational cycles over the indicated humidity range for the 50 micron thick piece of humidity sensing material; and FIG. 4 is a plot of sensor response as a function of relative humidity for the 50 micron thick piece of humidity sensing material at two different temperatures over the indicated humidity range.

DESCRIPTION OF THE PREFERRED EMBODIMENT(S)

The present invention is a method for making a humidity sensing material that can be readily incorporated into a sensing device that will have two electrodes coupled to the humidity sensing material to facilitate the "reading" of changing electrical properties (e.g., capacitance) experienced by the material when an environment's humidity changes. As used herein, the word "humidity" refers to an environment's relative humidity that is a percentage ratio of actual water vapor pressure to the saturation vapor pressure as is well understood in the art.

The humidity sensing material resulting from the method described herein is a lanthanum-doped barium titanate-based ceramic material. The process described herein for manufacturing this material produces a material that is highly sensitive to changes in humidity. In tests of the material in a sensing device, the material has exhibited rapid and large changes in capacitance for just a small amount of humidity change. The material provides this type of sensitivity even when only a small amount is used (e.g., a 0.06 square centimeter footprint or less with thicknesses of only 1-50 microns). Accordingly, the humidity sensing material produced by the present invention is ideally suited for use in sensitive hygrometers used in semiconductor manufacturing facilities, electronic weather stations, aboard aerospace vehicles, or any application requiring fast and sensitive responses to humidity changes using a low mass and small footprint sensing device.

Figure 1:
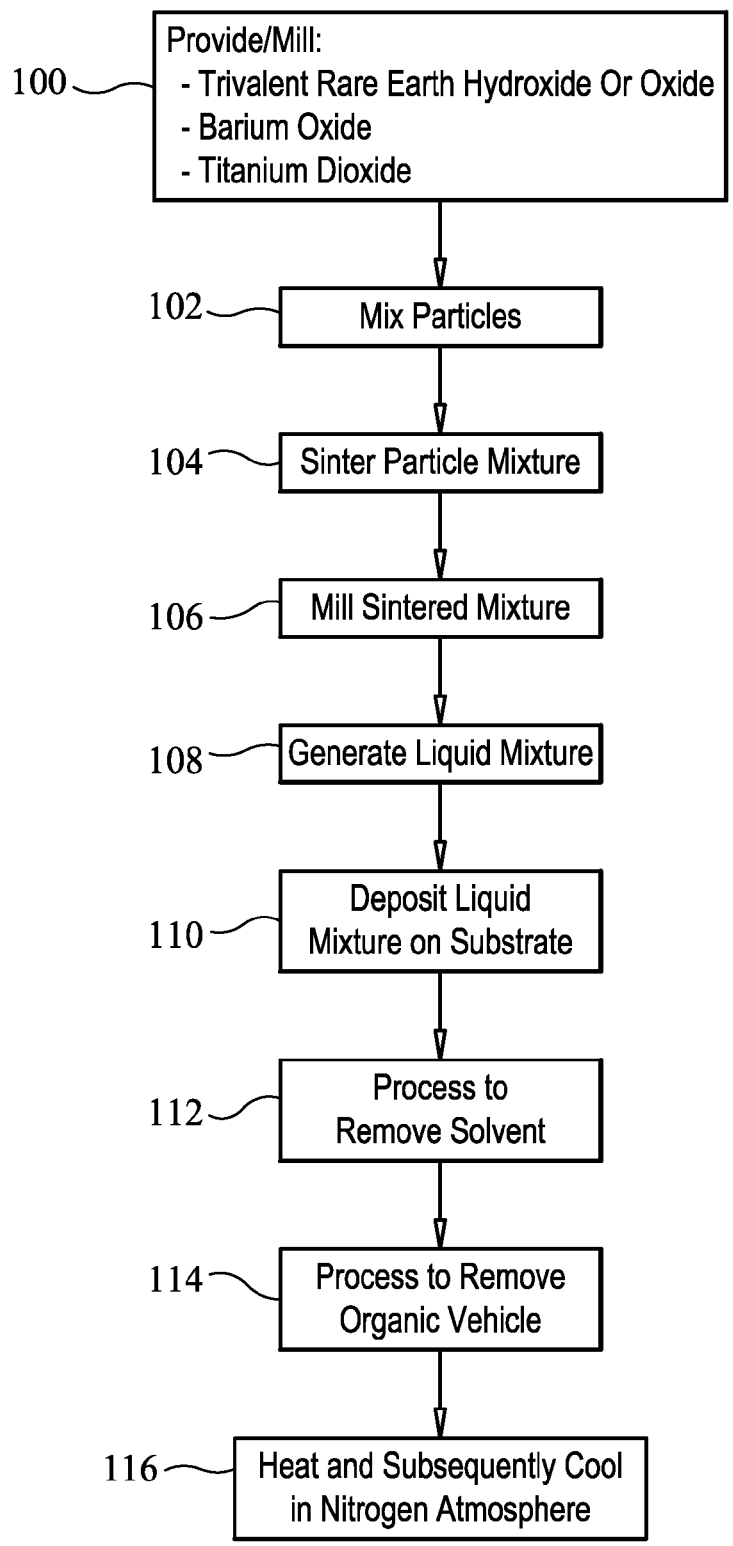
FIG. 1 is a flow diagram of a method of manufacturing a humidity sensing material in accordance with an embodiment of the present invention.

Referring now to the drawings and more particularly to FIG. 1 a flow diagram is shown of a method for manufacturing a humidity sensing material in accordance with an embodiment of the present invention. While the method will be described relative to a specific embodiment, it is to be understood that additional embodiments are enabled by the following description. In general, the base material components used by the present invention include a trivalent rare earth hydroxide or oxide, barium oxide, and titanium dioxide. For the embodiment described below, the trivalent rare earth hydroxide, lanthanum hydroxide, is used.

At step 100, each of the base materials (i.e., lanthanum hydroxide, barium oxide, and titanium dioxide) is milled to provide particle forms thereof having an average grain diameter of 50-700 nanometers. It is to be understood that milling in step 100 could be omitted if the base materials were already available in the specified particle forms. At step 102, the base materials are mixed together in the following weight percent proportions:

0.7-5.0 weight percent lanthanum hydroxide,
60-65 weight percent barium oxide, and
a remaining weight percent provided by titanium dioxide.

The above-described particle mixture is heated at step 104 to a temperature in a range of 1000-1300° Celsius (C) from 4-10 hours in order to sinter the particle mixture while limiting grain growth. A heat ramp up rate of approximately 5° C. can be used. The resulting solid sintered base material mixture is cooled to an ambient temperature where a cooling ramp rate of approximately 5° C. can be used. The resulting cooled sintered mixture is then milled at step 106 to produce milled particles having diameters of 50-700 nanometers.

The above-described sintered/milled particles are then used at step 108 to produce a liquid mixture. As will be described further below, the liquid mixture can be deposited on a substrate that can include an electrode when the humidity sensing material of the present invention is to be simultaneously fabricated with elements to incorporate the humidity sensing material as part of a humidity sensor.

The liquid mixture includes the following weight percent proportions:

50-70 weight percent of the above-described sintered/milled particles,
5-15 weight percent of glass particles (e.g., lead germinate, zinc borate) having particle sizes ranging from 0.5 to 10 micrometers,
0.1-5.0 weight percent of an organic surfactant such as surfactants made from phosphate esters,
5-25 weight percent of a solvent such as ester alcohol, terpineol, or butyl carbitol,
5-25 weight percent of an organic vehicle such as ethyl cellulose, and
1-5 weight percent of an alkali hydroxide such as potassium hydroxide, sodium hydroxide, rubidium hydroxide, or lithium hydroxide.

The liquid mixture from step 108 is deposited on a substrate at step 110. The humidity sensing material produced in accordance with the present invention can function well even at thicknesses on the order of 1 micrometer. In general, the humidity sensing material can range in thickness from 1 micrometer to 50 micrometers or more. The liquid mixture on the substrate is processed to achieve a desired thickness. A single or multiple layers of the liquid mixture could be deposited on the substrate. For example, a single layer at a desired thickness can be achieved by using a screen of predetermined size. Such screens and their use are well known in the art of semiconductor "printing". The substrate and liquid layer are then dried at step 112 to remove the solvent. Multiple layer thicknesses can also be developed using a repetitive series of depositing a liquid layer on the substrate and then processing the substrate and liquid layer to remove the solvent from the liquid layer(s). For single or multiple layer processes, solvent can be removed by heating the substrate along with any previously dried layer and current liquid layer thereon in an air environment to a temperature of 120-150° C. for a time period of 15-30 minutes. The above liquid mixture deposition and drying can be carried out as many times as needed to achieve a desired thickness for the ultimate material specimen.

The specimen generated by step 112 can be further processed at step 114 to remove the organic vehicle (e.g., ethyl cellulose) by a heating and cooling cycle. For example, the substrate and single or multiple layer specimen can be gradually heated to a temperature in a range of 280-350° C. A suitable gradual heating rate should not exceed 15° C. per minute. The heating temperature of 280-350° C. should be maintained for a time period of 4-72 hours to assure removal of the organic vehicle. Following heating to 280-350° C., the substrate with specimen thereon is cooled to an ambient temperature. For example, cooling can be controlled to a rate of 5-10° C. per minute until the specimen achieves a temperature in an ambient temperature in a range of 20-25° C. As a result of processing steps 112 and 114, all liquid portions of the liquid mixture deposited in step 110 are removed yielding a solid material specimen.

The solid material specimen resulting from steps 112 and 114 is further processed at step 116 in accordance with at least one heating cycle followed by a corresponding cooling cycle. In each such heating cycle, the substrate and solid material specimen are heated to a temperature in a range of 850-900° C. for a time period not to exceed 15 minutes. Such heating allows the glass particles to re-flow in the layer(s) so that individual particles hold together. Following such heating, the substrate and solid material specimen are cooled to an ambient temperature (i.e., 20-25° C.) in a nitrogen atmosphere that contains less than 25 parts per million of oxygen.

Figure 2:
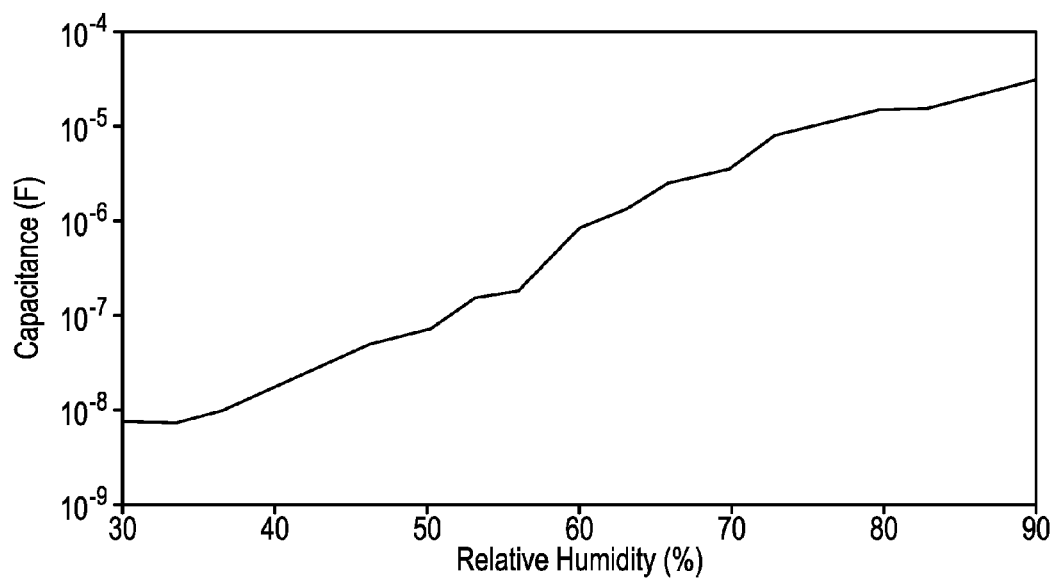
FIG. 2 is a plot of capacitance as a function of relative humidity for a 50 micron thick piece of humidity sensing material fabricated in accordance with an embodiment of the present invention.

The resulting humidity sensing material produced in accordance with the above-described processing steps is a lanthanum-doped barium titanate-based ceramic material. Tests of a variety of thicknesses and surface areas of the humidity sensing material have shown the material to be highly-sensitive to even small changes in humidity over a wide range of relative humidity. For example, FIG. 2 illustrates test results for an approximately 50 micron thick piece of the humidity sensing material made in accordance with the process described above. For the exemplary material, the following proportions were used in the above-described step 102:

0.8 weight percent lanthanum hydroxide,
65 weight percent barium oxide, and
34.2 weight percent by titanium dioxide.

For the exemplary material, the following proportions were used in the above-described step 108:

61.9 weight percent of the above-described particle mixture following processing in accordance with steps 104 and 106,
6.8 weight percent of lead germinate glass particles,
1.0 weight percent of a phosphate ester organic surfactant,
14.1 weight percent of an ester alcohol solvent,
14.1 weight percent of an ethyl cellulose organic vehicle, and
2.1 weight percent of potassium hydroxide serving as the alkali hydroxide co-dopant.

The resulting humidity sensing material was sandwiched between two silver palladium electrodes to thereby define a capacitor.

As evidenced by the test results shown in FIG. 2, capacitance changes by several orders of magnitude over the standard relative humidity range of 30-90%. The log-linear behavior of the sensing material facilitates calibration of the relative humidity plot over a large humidity range. Further-more, the large change in capacitance over a broad range of humidity translates to high sensitivity and accuracy.

The test results illustrated in FIG. 2 were achieved at a test frequency of 1 kHz. Given that 1 kHz is the industry standard frequency used to measure capacitive sensor performance, it is clear that the humidity sensing material fabricated in accordance with the present invention provides a high level of confidence in performance.

Another measure of capacitive sensor performance is defined as repeatability or the consistency of results over multiple cycles of the sensor. Repeatability tests for the above-described exemplary humidity sensing material are shown in FIG. 3 where sensor response is plotted as a function of relative humidity. As the sensor (incorporating the exemplary humidity sensing material) was cycled from 20% to 90% relative humidity multiple times, capacitance was recorded. For each cycle, the measured capacitance data was identical (or nearly so) thereby yielding the single curve illustrated in FIG. 3. That is, the humidity sensing material fabricated in accordance with the present invention yielded no appreciable drift over multiple operational cycles spanning a broad range of relative humidity.

The sensor incorporating the above-described exemplary humidity sensing material was also tested at temperatures of 25° C. and 85° C. with the resultant sensor response as a function of relative humidity being plotted in FIG. 4. Specifically, the test results at 25° C. are represented by curve 100 and the test results at 85° C. are represented by curve 102. Since the curves are nearly identical in shape, calibration of a sensor incorporating the exemplary humidity sensing material is simplified and need not be limited to just one temperature condition.

The present fabrication method can be used to fabricate other humidity sensing material formulations. For example, another highly-sensitive humidity sensing material using the trivalent rare earth lanthanum hydroxide and fabricated in accordance with the present invention used the following proportions in the above-described step 102:

4 weight percent lanthanum hydroxide,
62 weight percent barium oxide, and
34 weight percent by titanium dioxide.

Still another highly-sensitive humidity sensing material was made using the trivalent rare earth lanthanum oxide. The material was fabricated in accordance with the present invention and used the following proportions in the above-described step 102:

0.7 weight percent lanthanum oxide,
65.1 weight percent barium oxide, and
34.2 weight percent by titanium dioxide.

As mentioned above, the humidity sensing material fabrication process of the present invention can incorporate steps that integrate the humidity sensing material into a humidity sensor in which the humidity sensing material is sandwiched between two electrodes. For example, prior to the above-described process step 110 where the liquid mixture was deposited on a substrate, a low-resistance (e.g., resistance between 1 milliohm and 10 ohms) electrode could be deposited and sintered onto the substrate in ways well-known in the art. Then, in process step 110, the liquid mixture would fully cover the electrode on the substrate and processing would continue as described above. The second or top electrode would then be deposited on the solid material specimen resulting from step 116, and the heating/cooling process of step 116 would be repeated.

The advantages of the present invention are numerous. The process produces a highly-sensitive humidity sensing material that can be readily incorporated into a variety of electronics devices. Sensitivity spans over a broad range of relative humidity levels. Further, the highly-sensitive response can be achieved with very small pieces (i.e., in terms of thickness and surface area) of the material.

Although the invention has been described relative to specific embodiments thereof, there are numerous variations and modifications that will be readily apparent to those skilled in the art in light of the above teachings. For example, other trivalent rare earth hydroxides or oxides could be based on the rare earth elements neodymium, samarium, europium, gadolinium and dysprosium. It is therefore to be understood that, within the scope of the appended claims, the invention may be practiced other than as specifically described.

What is claimed as new and desired to be secured by Letters Patent of the United States is:

The invention claimed is:
1. A method of manufacturing a humidity sensing material, comprising the steps of:
    providing particles of lanthanum hydroxide having an average grain diameter of 50-700 nanometers, particles of barium oxide having an average grain diameter of 50-700 nanometers, and particles of titanium dioxide having an average grain diameter of 50-700 nanometers;
    mixing 0.7-5.0 weight percent of said particles of lanthanum hydroxide, 60-65 weight percent of said particles of barium oxide, and a remaining weight percent of said particles of titanium dioxide, wherein a mixture of particles is generated;
    heating said mixture of particles to a temperature in a range of 1000-1300° C. wherein a sintered mixture is generated;
    milling said sintered mixture to generate milled particles having diameters of 50-700 nanometers;
    mixing 50-70 weight percent of said milled particles with
        5-15 weight percent of glass particles having a particle size of 0.5-10 micrometers,
        0.1-5.0 weight percent of an organic surfactant,
        5-25 weight percent of a solvent,
        5-25 weight percent of an organic vehicle, and
        1-5 weight percent of an alkali hydroxide,
    wherein a liquid mixture is generated;
    depositing a layer of said liquid mixture onto a substrate; and
    processing said substrate with said layer thereon to remove liquid portions of said liquid mixture, wherein said step of processing includes at least one cycle of heating said layer to a temperature in a range of 850-900° C. followed by at least one cycle of cooling said layer in a nitrogen atmosphere containing less than 25 parts per million of oxygen.

2. A method according to claim 1, wherein said step of heating said mixture of particles occurs in air.

3. A method according to claim 1, wherein said step of heating said mixture of particles occurs in a vacuum.

4. A method according to claim 1, wherein said layer is 1-50 micrometers in thickness.

5. A method according to claim 1, wherein said organic surfactant is selected from the group consisting of phosphate esters.

6. A method according to claim 1, wherein said solvent is selected from the group consisting of ester alcohol, terpineol, and butyl carbitol.

7. A method according to claim 1, wherein said organic vehicle comprises ethyl cellulose.

8. A method according to claim 1, wherein said alkali hydroxide is selected from the group consisting of potassium hydroxide, sodium hydroxide, rubidium hydroxide and lithium hydroxide.

9. A method according to claim 1, wherein said glass particles are selected from the group consisting of lead germinate glass particles and zinc borate glass particles.

10. A method of manufacturing a humidity sensing material, comprising the steps of:
providing particles of lanthanum hydroxide having an average grain diameter of 50-700 nanometers, particles of barium oxide having an average grain diameter of 50-700 nanometers, and particles of titanium dioxide having an average grain diameter of 50-700 nanometers;
mixing 0.7-5.0 weight percent of said particles of lanthanum hydroxide, 60-65 weight percent of said particles of barium oxide, and a remaining weight percent of said particles of titanium dioxide, wherein a mixture of particles is generated;
heating said mixture of particles to a temperature in a range of 1000-1300° C. wherein a sintered mixture is generated;
milling said sintered mixture to generate milled particles having diameters of 50-700 nanometers;
mixing 50-70 weight percent of said milled particles with 5-15 weight percent of glass particles having a particle size of 0.5-10 micrometers,
0.1-5.0 weight percent of an organic surfactant,
5-25 weight percent of a solvent,
5-25 weight percent of an organic vehicle, and
1-5 weight percent of an alkali hydroxide,
wherein a liquid mixture is generated;
depositing a layer of said liquid mixture onto a substrate;
heating said substrate with said layer thereon to a temperature in a range of 280-350° C. for a period of time in a range of 4-72 hours;
placing said substrate with said layer thereon in a cooling environment for cooling said layer at a cooling rate of 5-10° C. per minute and for a period of time sufficient to allow said layer to cool to a cooled temperature in a range of 20-25° C.;
re-heating said substrate with said layer thereon to a temperature in a range of 850-900° C. for a time period not to exceed 15 minutes; and
placing said substrate with said layer thereon in a nitrogen-atmosphere environment for cooling said layer at a cooling rate of 5-10° C. per minute and for a period of time sufficient to allow said layer to cool to said cooled temperature, wherein said nitrogen-atmosphere environment contains less than 25 parts per million of oxygen.

11. A method according to claim 10, wherein said step of heating said mixture of particles occurs in air.

12. A method according to claim 10, wherein said step of heating said mixture of particles occurs in a vacuum.

13. A method according to claim 10, wherein said layer is 1-50 micrometers in thickness.

14. A method according to claim 10, wherein said organic surfactant is selected from the group consisting of phosphate esters.

15. A method according to claim 10, wherein said solvent is selected from the group consisting of ester alcohol, terpineol, and butyl carbitol.

16. A method according to claim 10, wherein said organic vehicle comprises ethyl cellulose.

17. A method according to claim 10, wherein said alkali hydroxide is selected from the group consisting of potassium hydroxide, sodium hydroxide, rubidium hydroxide and lithium hydroxide.

18. A method according to claim 10, wherein said glass particles are selected from the group consisting of lead germinate glass particles and zinc borate glass particles.

19. A method of manufacturing a humidity sensing material, comprising the steps of:
providing particles of lanthanum hydroxide having an average grain diameter of 50-700 nanometers, particles of barium oxide having an average grain diameter of 50-700 nanometers, and particles of titanium dioxide having an average grain diameter of 50-700 nanometers;
mixing 0.7-5.0 weight percent of said particles of lanthanum hydroxide, 60-65 weight percent of said particles of barium oxide, and a remaining weight percent of said particles of titanium dioxide, wherein a mixture of particles is generated;
heating said mixture of particles to a temperature in a range of 1000-1300° C. wherein a sintered mixture is generated;
milling said sintered mixture to generate milled particles having diameters of 50-700 nanometers;
mixing 50-70 weight percent of said milled particles with 5-15 weight percent of glass particles having a particle size of 0.5-10 micrometers,
0.1-5.0 weight percent of an organic surfactant,
5-25 weight percent of a solvent,
5-25 weight percent of an organic vehicle, and
1-5 weight percent of an alkali hydroxide,
wherein a liquid mixture is generated;
depositing at least one layer of said liquid mixture onto a substrate;
processing said substrate with said at least one layer thereon to remove liquid portions of said liquid mixture from said at least one layer wherein a solid material specimen remains on said substrate; and
processing said substrate with said solid material specimen thereon to include at least one cycle of heating said solid material specimen to a temperature in a range of 850-900° C. followed by at least one cycle of cooling said solid material specimen in a nitrogen atmosphere containing less than 25 parts per million of oxygen.

20. A method according to claim 19, wherein said step of heating said mixture of particles occurs in air.

21. A method according to claim 19, wherein said step of heating said mixture of particles occurs in a vacuum.

22. A method according to claim 19, wherein said solid material specimen is 1-50 micrometers in thickness.

23. A method according to claim 19, wherein said organic surfactant is selected from the group consisting of phosphate esters.

24. A method according to claim 19, wherein said solvent is selected from the group consisting of ester alcohol, terpineol, and butyl carbitol.

25. A method according to claim 19, wherein said organic vehicle comprises ethyl cellulose.

26. A method according to claim 19, wherein said alkali hydroxide is selected from the group consisting of potassium hydroxide, sodium hydroxide, rubidium hydroxide and lithium hydroxide.

27. A method according to claim 19, wherein said glass particles are selected from the group consisting of lead germinate glass particles and zinc borate glass particles.

* * * * *